(12) United States Patent
Dabrowiak et al.

(10) Patent No.: US 11,033,424 B2
(45) Date of Patent: Jun. 15, 2021

(54) FLUID CASSETTE WITH TENSIONED POLYMERIC MEMBRANES FOR PATIENT HEAT EXCHANGE SYSTEM

(71) Applicant: Zoll Circulation, Inc., San Jose, CA (US)

(72) Inventors: Jeremy Thomas Dabrowiak, Redwood City, CA (US); Christoph Matthias Pistor, Santa Cruz, CA (US); Craig Wendell Pendry, Milpitas, CA (US); Christo Pamichev, Cupertino, CA (US)

(73) Assignee: Zoll Circulation, Inc., San Jose, CA (US)

( * ) Notice: Subject to any disclaimer, the term of this patent is extended or adjusted under 35 U.S.C. 154(b) by 0 days.

(21) Appl. No.: 14/180,613

(22) Filed: Feb. 14, 2014

(65) Prior Publication Data
US 2015/0230973 A1 Aug. 20, 2015

(51) Int. Cl.
*A61B 7/00* (2006.01)
*A61F 7/00* (2006.01)
*A61M 5/44* (2006.01)
*A61F 7/10* (2006.01)
*A61F 7/12* (2006.01)

(52) U.S. Cl.
CPC ............. *A61F 7/0085* (2013.01); *A61M 5/44* (2013.01); *A61F 7/10* (2013.01); *A61F 2007/0056* (2013.01); *A61F 2007/126* (2013.01); *A61M 2205/12* (2013.01); *A61M 2205/127* (2013.01); *A61M 2205/366* (2013.01); *Y10T 29/4935* (2015.01)

(58) Field of Classification Search
CPC .......... A61F 7/0085; A61F 7/12; A61F 7/123; A61F 2007/0054–0058; A61F 2007/0091; A61F 2007/0092; A61F 2007/0098; A61F 2007/0244–026; A61F 2007/126
See application file for complete search history.

(56) References Cited

U.S. PATENT DOCUMENTS 1,459,112 A 6/1923 Mehl
1,726,761 A * 9/1929 Palmer .................... A61F 7/08
383/119

(Continued)

FOREIGN PATENT DOCUMENTS

CN 101090685 12/2007
DE 19531935 2/1997

(Continued)

OTHER PUBLICATIONS

Extra Packaging Corp, Polyurethane Properties and Characterisitics, accessed May 9, 2016 at http://www.extrapackaging.com/polyurethane/properites.php.*

(Continued)

*Primary Examiner* — Linda C Dvorak
*Assistant Examiner* — Ryan T Clark
(74) *Attorney, Agent, or Firm* — Fish & Richardson P.C.

(57) ABSTRACT

A working fluid cassette for an intravascular heat exchange catheter includes a frame holding two closely spaced, square polymeric membranes in tension. Working fluid from the catheter is directed between the membranes. The cassette is closely received between two refrigerant cold plates to exchange heat with the working fluid, which is circulated back to the catheter.

21 Claims, 6 Drawing Sheets

(56) References Cited

U.S. PATENT DOCUMENTS

| | | | |
|---|---|---|---|
| 1,857,031 A | 5/1932 | Schaffer | |
| 2,223,688 A | 12/1940 | Otoo | |
| 2,663,030 A | 12/1953 | Dahlberg | |
| 2,673,987 A | 4/1954 | Upshaw et al. | |
| 2,987,004 A | 6/1961 | Murray | |
| 3,140,716 A | 7/1964 | Harrison et al. | |
| 3,225,191 A | 12/1965 | Calhoun | |
| 3,228,465 A | 1/1966 | Vadot | |
| 3,369,549 A | 2/1968 | Armao | |
| 3,425,419 A | 2/1969 | Dato | |
| 3,504,674 A | 4/1970 | Swenson | |
| 3,726,269 A | 4/1973 | Webster, Jr. | |
| 3,744,555 A | 7/1973 | Fletcher et al. | |
| 3,751,077 A | 8/1973 | Hiszpanski | |
| 3,834,396 A | 9/1974 | Foster | |
| 3,937,224 A | 2/1976 | Uecker | |
| 3,945,063 A | 3/1976 | Matsuura | |
| 4,038,519 A | 7/1977 | Foucras | |
| 4,065,264 A | 12/1977 | Lewin | |
| 4,103,511 A | 8/1978 | Kress et al. | |
| 4,126,132 A | 11/1978 | Portner et al. | |
| 4,153,048 A | 5/1979 | Magrini | |
| 4,173,228 A | 11/1979 | Van Steenwyk et al. | |
| 4,181,132 A | 1/1980 | Parks | |
| 4,181,245 A * | 1/1980 | Garrett | A61M 5/16809 |
| | | | 222/450 |
| 4,259,961 A * | 4/1981 | Hood, III | A61F 7/10 |
| | | | 607/104 |
| 4,298,006 A | 11/1981 | Parks | |
| 4,459,468 A | 7/1984 | Bailey | |
| 4,532,414 A | 7/1985 | Shah et al. | |
| 4,552,516 A | 11/1985 | Stanley | |
| 4,554,793 A | 11/1985 | Harding, Jr. | |
| 4,558,996 A | 12/1985 | Becker | |
| 4,581,017 A | 4/1986 | Sahota | |
| 4,638,436 A | 1/1987 | Badger et al. | |
| 4,653,987 A | 3/1987 | Tsuji et al. | |
| 4,661,094 A | 4/1987 | Simpson | |
| 4,665,391 A | 5/1987 | Spani | |
| 4,672,962 A | 6/1987 | Hershenson | |
| 4,754,752 A | 7/1988 | Ginsburg et al. | |
| 4,787,388 A | 11/1988 | Hofmann | |
| 4,813,855 A | 3/1989 | Leveen et al. | |
| 4,849,196 A | 7/1989 | Yamada et al. | |
| 4,852,567 A | 8/1989 | Sinofsky | |
| 4,860,744 A | 8/1989 | Johnson et al. | |
| 4,869,250 A | 9/1989 | Bitterly | |
| 4,906,237 A | 3/1990 | Johansson et al. | |
| 4,925,376 A | 5/1990 | Kahler | |
| 4,941,475 A | 7/1990 | Williams et al. | |
| 5,080,089 A | 1/1992 | Mason et al. | |
| 5,092,841 A | 3/1992 | Spears | |
| 5,103,360 A | 4/1992 | Maeda | |
| 5,106,360 A | 4/1992 | Ishiwara et al. | |
| 5,174,285 A | 12/1992 | Fontenot | |
| 5,192,274 A | 3/1993 | Bierman | |
| 5,195,965 A | 3/1993 | Shantha | |
| 5,211,631 A | 5/1993 | Sheaff | |
| 5,263,925 A | 11/1993 | Gilmore et al. | |
| 5,269,758 A | 12/1993 | Taheri | |
| 5,281,215 A | 1/1994 | Milder | |
| 5,304,214 A | 4/1994 | DeFord et al. | |
| 5,342,301 A | 8/1994 | Saab | |
| 5,344,436 A | 9/1994 | Fontenot et al. | |
| 5,370,675 A | 12/1994 | Edwards et al. | |
| 5,383,856 A | 1/1995 | Bersin | |
| 5,391,030 A | 2/1995 | Lee | |
| 5,403,281 A | 4/1995 | O'Neill et al. | |
| 5,420,962 A | 5/1995 | Bakke | |
| 5,433,588 A | 7/1995 | Monk et al. | |
| 5,433,740 A | 7/1995 | Yamaguchi | |
| 5,437,673 A | 8/1995 | Baust et al. | |
| 5,458,639 A | 10/1995 | Tsukashima et al. | |
| 5,466,208 A | 11/1995 | Jackson | |
| 5,476,368 A | 12/1995 | Rabenau | |
| 5,486,207 A | 1/1996 | Mahawili | |
| 5,507,792 A * | 4/1996 | Mason | A61F 5/05816 |
| | | | 601/15 |
| 5,531,714 A | 7/1996 | Dahn et al. | |
| 5,531,776 A | 7/1996 | Ward et al. | |
| 5,624,392 A | 4/1997 | Saab | |
| 5,634,907 A | 6/1997 | Rani et al. | |
| 5,676,670 A | 10/1997 | Kim | |
| 5,693,344 A | 12/1997 | Knight | |
| 5,701,905 A | 12/1997 | Esch | |
| 5,706,889 A | 1/1998 | Bach et al. | |
| 5,709,564 A | 1/1998 | Yamada et al. | |
| 5,709,654 A | 1/1998 | Klatz et al. | |
| 5,716,386 A | 2/1998 | Ward et al. | |
| 5,730,720 A | 3/1998 | Sites et al. | |
| 5,733,319 A | 3/1998 | Neilson et al. | |
| 5,737,782 A | 4/1998 | Matsuura et al. | |
| 5,746,585 A | 5/1998 | McDunn | |
| 5,759,017 A | 6/1998 | Patton et al. | |
| 5,776,079 A | 7/1998 | Cope et al. | |
| 5,788,647 A | 8/1998 | Eggers | |
| 5,803,324 A | 9/1998 | Silberman | |
| 5,837,003 A | 11/1998 | Ginsburg | |
| 5,857,843 A | 1/1999 | Leason | |
| 5,862,675 A | 1/1999 | Scaringe et al. | |
| 5,875,282 A | 2/1999 | Jordan | |
| 5,879,329 A | 3/1999 | Ginsburg | |
| 5,895,418 A | 4/1999 | Saringer | |
| 5,908,407 A | 6/1999 | Frazee et al. | |
| 5,957,963 A | 9/1999 | Dobak, III | |
| 5,980,561 A | 11/1999 | Kolen et al. | |
| 5,989,238 A | 11/1999 | Ginsburg | |
| 6,019,783 A | 2/2000 | Philips et al. | |
| 6,042,559 A | 3/2000 | Dobak, III | |
| 6,051,019 A | 4/2000 | Dobak, III | |
| 6,059,825 A | 5/2000 | Hobbs et al. | |
| 6,096,068 A | 8/2000 | Dobak, III et al. | |
| 6,110,139 A | 8/2000 | Loubser | |
| 6,110,168 A | 8/2000 | Ginsburg | |
| 6,117,065 A | 9/2000 | Hastings et al. | |
| 6,117,105 A | 9/2000 | Bresnaham et al. | |
| 6,124,452 A | 9/2000 | Di Magno | |
| 6,126,684 A | 10/2000 | Gobin et al. | |
| 6,146,141 A | 11/2000 | Schumann | |
| 6,146,411 A | 11/2000 | Noda et al. | |
| 6,148,634 A | 11/2000 | Sherwood | |
| 6,149,670 A | 11/2000 | Worthen et al. | |
| 6,149,673 A | 11/2000 | Ginsburg | |
| 6,149,676 A | 11/2000 | Ginsburg | |
| 6,149,677 A | 11/2000 | Dobak, III | |
| 6,149,806 A | 11/2000 | Baer | |
| 6,165,207 A | 12/2000 | Balding | |
| 6,188,930 B1 | 2/2001 | Carson | |
| 6,197,045 B1 | 3/2001 | Carson | |
| 6,224,624 B1 | 5/2001 | Lasheras | |
| 6,231,594 B1 | 5/2001 | Dae | |
| 6,231,595 B1 | 5/2001 | Dobak | |
| 6,235,048 B1 | 5/2001 | Dobak | |
| 6,238,428 B1 | 5/2001 | Werneth | |
| 6,245,095 B1 | 6/2001 | Dobak | |
| 6,251,129 B1 | 6/2001 | Dobak | |
| 6,251,130 B1 | 6/2001 | Dobak | |
| 6,254,626 B1 | 7/2001 | Dobak | |
| 6,261,312 B1 | 7/2001 | Dobak | |
| 6,264,679 B1 | 7/2001 | Keller | |
| 6,283,940 B1 | 9/2001 | Mulholland | |
| 6,287,326 B1 | 9/2001 | Pecor | |
| 6,290,717 B1 | 9/2001 | Philips | |
| 6,299,599 B1 | 10/2001 | Pham et al. | |
| 6,306,161 B1 | 10/2001 | Ginsburg | |
| 6,312,452 B1 | 11/2001 | Dobak | |
| 6,325,818 B1 | 12/2001 | Werneth | |
| 6,338,727 B1 | 1/2002 | Noda et al. | |
| 6,364,899 B1 | 4/2002 | Dobak | |
| 6,368,304 B1 | 4/2002 | Aliberto | |
| 6,375,674 B1 | 4/2002 | Carson | |
| 6,379,378 B1 | 4/2002 | Werneth | |
| 6,383,144 B1 | 5/2002 | Mooney et al. | |
| 6,383,210 B1 | 5/2002 | Magers | |

(56) References Cited

U.S. PATENT DOCUMENTS

| | | |
|---|---|---|
| 6,393,320 B2 | 5/2002 | Lasersohn |
| 6,405,080 B1 | 6/2002 | Lasersohn |
| 6,409,747 B1 | 6/2002 | Gobin et al. |
| 6,416,533 B1 | 7/2002 | Gobin et al. |
| 6,419,643 B1 | 7/2002 | Shimada |
| 6,428,563 B1 | 8/2002 | Keller |
| 6,450,990 B1 | 9/2002 | Walker et al. |
| 6,461,379 B1 | 10/2002 | Carson |
| 6,464,666 B1 | 10/2002 | Augustine et al. |
| 6,464,716 B1 | 10/2002 | Dobak, III et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | Le Pivert |
| 6,554,791 B1 | 4/2003 | Cartledge et al. |
| 6,582,387 B2 | 6/2003 | Derek |
| 6,605,106 B2 | 8/2003 | Schwartz |
| 6,610,083 B2 | 8/2003 | Keller et al. |
| 6,613,280 B2 | 9/2003 | Myrick |
| 6,620,187 B2 | 9/2003 | Carson et al. |
| 6,620,188 B1 | 9/2003 | Ginsburg et al. |
| 6,620,189 B1 | 9/2003 | Machold |
| 6,622,542 B2 | 9/2003 | Derek |
| 6,624,679 B2 | 9/2003 | Tomaivolo et al. |
| 6,635,076 B1 | 10/2003 | Ginsburg |
| 6,635,079 B2 | 10/2003 | Ginsburg |
| 6,645,232 B2 | 11/2003 | Carson et al. |
| 6,648,905 B2 | 11/2003 | Hoglund |
| 6,660,027 B2 | 12/2003 | Gruszecki |
| 6,669,715 B2 | 12/2003 | Hoglund |
| 6,673,098 B1 * | 1/2004 | Machold .............. A61F 7/12 607/104 |
| 6,675,835 B2 | 1/2004 | Gerner |
| 6,679,906 B2 | 1/2004 | Hammack et al. |
| 6,685,731 B2 | 2/2004 | Kushnir et al. |
| 6,685,733 B1 | 2/2004 | Dae et al. |
| 6,692,518 B2 | 2/2004 | Carson |
| 6,695,874 B2 | 2/2004 | Machold et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,733,495 B1 | 5/2004 | Bek |
| 6,740,109 B2 | 5/2004 | Dobak, III |
| 6,743,201 B1 | 6/2004 | Donig et al. |
| 6,764,391 B1 | 7/2004 | Grant |
| 6,799,063 B2 | 9/2004 | Carson |
| 6,799,342 B1 | 10/2004 | Jarmon |
| 6,802,855 B2 | 10/2004 | Ellingboe |
| 6,818,012 B2 | 11/2004 | Ellingboe |
| 6,827,728 B2 | 12/2004 | Ellingboe |
| 6,843,099 B2 | 1/2005 | Derek |
| 6,843,800 B1 | 1/2005 | Dobak, III |
| 6,878,156 B1 | 4/2005 | Noda |
| 6,887,263 B2 | 5/2005 | Bleam et al. |
| 6,890,347 B2 | 5/2005 | Machold |
| 6,893,419 B2 | 5/2005 | Noda et al. |
| 6,969,399 B2 | 11/2005 | Schock et al. |
| 6,974,435 B2 | 12/2005 | Derek |
| 6,997,942 B2 | 2/2006 | Machold |
| 7,070,612 B1 | 7/2006 | Collins et al. |
| 7,104,769 B2 | 9/2006 | Davis |
| 7,140,850 B2 | 11/2006 | Otis |
| 7,175,649 B2 | 2/2007 | Machold |
| 7,181,927 B2 | 2/2007 | Collins |
| 7,211,106 B2 | 5/2007 | Dobak |
| 7,247,165 B2 | 7/2007 | Machold |
| 7,258,662 B2 | 8/2007 | Machold |
| 7,357,786 B1 * | 4/2008 | Bakke .............. A61F 7/12 604/114 |
| 7,377,935 B2 | 5/2008 | Schock |
| 7,510,569 B2 | 3/2009 | Dae et al. |
| 7,516,909 B2 | 4/2009 | Kaligain |
| 7,645,127 B2 | 1/2010 | Hagen |
| 7,658,755 B2 | 2/2010 | Machold |
| 7,666,215 B2 | 3/2010 | Callister et al. |
| 7,713,036 B2 | 5/2010 | Kojima et al. |
| 7,820,102 B2 | 10/2010 | Myrick |
| 7,822,485 B2 | 10/2010 | Collins |
| 7,846,193 B2 | 12/2010 | Dae et al. |
| 7,857,781 B2 | 12/2010 | Noda et al. |
| 7,892,269 B2 | 2/2011 | Collins et al. |
| 7,879,077 B2 | 3/2011 | Machold |
| 7,914,564 B2 | 3/2011 | Magers |
| 7,959,657 B1 | 6/2011 | Harsy |
| 7,963,986 B2 | 6/2011 | Machold |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,128,384 B2 | 3/2012 | Mou |
| 8,177,824 B2 | 5/2012 | Machold |
| 8,226,605 B2 | 7/2012 | Faries, Jr. et al. |
| 8,246,669 B2 | 8/2012 | Machold |
| 8,272,857 B2 | 9/2012 | Norman et al. |
| 8,366,667 B2 | 2/2013 | Chan |
| 8,551,151 B2 | 10/2013 | Machold |
| 8,740,959 B2 | 6/2014 | Machold |
| 8,784,464 B2 | 7/2014 | Machold |
| 8,888,729 B2 | 11/2014 | Noda |
| 9,345,614 B2 | 5/2016 | Schaefer |
| 9,474,644 B2 | 10/2016 | Dabrowiak |
| 9,492,633 B2 | 11/2016 | Dabrowiak |
| 9,675,756 B2 | 6/2017 | Kamen |
| 10,022,265 B2 | 7/2018 | Pamichev |
| 10,085,880 B2 | 10/2018 | Machold |
| 2001/0031946 A1 | 10/2001 | Walker et al. |
| 2001/0047196 A1 | 11/2001 | Ginsburg et al. |
| 2002/0004675 A1 | 1/2002 | Lasheras |
| 2002/0013569 A1 | 1/2002 | Sterman et al. |
| 2002/0022823 A1 | 2/2002 | Luo et al. |
| 2002/0096311 A1 | 7/2002 | Kushnir |
| 2002/0117559 A1 | 8/2002 | Kaligian |
| 2002/0134134 A1 | 9/2002 | Derek |
| 2002/0136662 A1 | 9/2002 | Myrick |
| 2002/0138034 A1 | 9/2002 | Derek |
| 2002/0145525 A1 | 10/2002 | Friedman et al. |
| 2002/0183692 A1 | 12/2002 | Callister |
| 2002/0198579 A1 | 12/2002 | Khanna |
| 2003/0036495 A1 | 2/2003 | Datta |
| 2003/0041911 A1 | 3/2003 | Gerner |
| 2003/0062090 A1 | 4/2003 | Secondo |
| 2003/0114795 A1 | 6/2003 | Durward |
| 2003/0135252 A1 | 7/2003 | Machold |
| 2003/0036496 A1 | 12/2003 | Samson et al. |
| 2003/0236496 A1 | 12/2003 | Elsner |
| 2004/0013566 A1 | 1/2004 | Myrick |
| 2004/0019319 A1 | 1/2004 | Derek |
| 2004/0024437 A1 | 2/2004 | Machold |
| 2004/0026068 A1 * | 2/2004 | Schmidt .............. A61M 5/44 165/46 |
| 2004/0089050 A1 | 5/2004 | Derek |
| 2004/0089058 A1 | 5/2004 | De Hann et al. |
| 2004/0102825 A1 | 5/2004 | Daoud |
| 2004/0104018 A1 | 6/2004 | Hugh et al. |
| 2004/0143311 A1 | 7/2004 | Machold |
| 2004/0154374 A1 | 8/2004 | Derek |
| 2004/0171935 A1 | 9/2004 | Van Creveld |
| 2004/0190255 A1 | 9/2004 | Cheon |
| 2004/0199230 A1 | 10/2004 | Yon |
| 2004/0210231 A1 | 10/2004 | Boucher et al. |
| 2004/0244371 A1 | 12/2004 | Takumori |
| 2004/0267340 A1 | 12/2004 | Cioanta |
| 2005/0065584 A1 | 3/2005 | Schiff |
| 2005/0137662 A1 | 6/2005 | Morris |
| 2005/0156744 A1 | 7/2005 | Pires |
| 2005/0209658 A1 | 9/2005 | Machold |
| 2006/0030917 A1 | 2/2006 | Eccleston |
| 2006/0064146 A1 | 3/2006 | Collins |
| 2006/0069418 A1 | 3/2006 | Schock et al. |
| 2006/0122673 A1 | 6/2006 | Callister et al. |
| 2006/0210424 A1 | 9/2006 | Mallett et al. |
| 2006/0241335 A1 | 10/2006 | Benkowski |

(56) References Cited

U.S. PATENT DOCUMENTS

| | | |
|---|---|---|
| 2006/0253095 A1 | 11/2006 | Stull |
| 2006/0293734 A1* | 12/2006 | Scott ................... A61F 7/12 607/105 |
| 2007/0007640 A1 | 1/2007 | Harnden et al. |
| 2007/0076401 A1 | 4/2007 | Carrez et al. |
| 2007/0093710 A1 | 4/2007 | Maschke |
| 2007/0156006 A1 | 7/2007 | Smith |
| 2007/0173759 A1 | 7/2007 | Augustine |
| 2007/0191918 A1 | 8/2007 | Machold |
| 2007/0203552 A1 | 8/2007 | Machold |
| 2007/0293919 A1 | 12/2007 | Machold |
| 2008/0026068 A1 | 1/2008 | Brown et al. |
| 2008/0082051 A1 | 4/2008 | Miller |
| 2008/0114430 A1 | 5/2008 | Collins |
| 2008/0119916 A1 | 5/2008 | Choucair |
| 2008/0230530 A1 | 9/2008 | Augustine et al. |
| 2008/0262409 A1 | 10/2008 | Derrico et al. |
| 2008/0267599 A1* | 10/2008 | Arnold ................. A61F 7/0085 392/470 |
| 2008/0269663 A1 | 10/2008 | Arnold |
| 2009/0065565 A1 | 3/2009 | Cao |
| 2009/0099518 A1 | 4/2009 | Magers |
| 2009/0247963 A1 | 10/2009 | Bleam et al. |
| 2009/0299287 A1 | 12/2009 | Carson et al. |
| 2010/0036486 A1 | 2/2010 | Mazur |
| 2010/0049119 A1 | 2/2010 | Norman et al. |
| 2010/0082000 A1 | 4/2010 | Honeck |
| 2010/0129248 A1 | 5/2010 | Mou |
| 2010/0204765 A1 | 8/2010 | Hall |
| 2010/0256601 A1 | 10/2010 | Lippert |
| 2011/0022136 A1 | 1/2011 | Scott et al. |
| 2011/0046551 A1* | 2/2011 | Augustine ............ A61F 7/0085 604/113 |
| 2011/0137249 A1 | 6/2011 | Collins et al. |
| 2011/0184253 A1 | 7/2011 | Archer et al. |
| 2011/0208276 A1 | 8/2011 | Machold |
| 2011/0208277 A1 | 8/2011 | Machold |
| 2011/0208278 A1 | 8/2011 | Machold et al. |
| 2011/0213305 A1 | 9/2011 | Jönsson et al. |
| 2012/0095536 A1 | 4/2012 | Machold |
| 2012/0100023 A1 | 4/2012 | Hanazuka |
| 2012/0158103 A1 | 6/2012 | Bledsoe |
| 2012/0226338 A1 | 9/2012 | Machold |
| 2013/0071270 A1 | 3/2013 | Zupp |
| 2013/0079855 A1 | 3/2013 | Helkowski |
| 2013/0079856 A1 | 3/2013 | Dabrowiak |
| 2013/0090708 A1 | 4/2013 | Dabrowiak |
| 2013/0098880 A1 | 4/2013 | Korolev |
| 2013/0172805 A1 | 7/2013 | Truckai |
| 2013/0178923 A1 | 7/2013 | Dabrowiak |
| 2013/0331774 A1* | 12/2013 | Farrell ................... A61M 1/28 604/28 |
| 2013/0337732 A1 | 12/2013 | Nilliams |
| 2014/0081202 A1 | 3/2014 | Tsoukalis |
| 2014/0094880 A1 | 4/2014 | Lim |
| 2014/0094882 A1 | 4/2014 | Lim |
| 2014/0094883 A1 | 4/2014 | Lim |
| 2014/0276792 A1 | 9/2014 | Kaveckis |
| 2014/0277302 A1 | 9/2014 | Weber |
| 2014/0364928 A1 | 12/2014 | Machold |
| 2015/0223974 A1 | 8/2015 | Dabrowiak |
| 2015/0230974 A1 | 8/2015 | Pistor |
| 2015/0230975 A1 | 8/2015 | Dabrowiak |
| 2015/0314055 A1 | 11/2015 | Hogard |
| 2016/0022477 A1 | 1/2016 | Schaefer |
| 2016/0089184 A1 | 3/2016 | Truckai |
| 2016/0166758 A1 | 6/2016 | Norman et al. |
| 2016/0228291 A1 | 8/2016 | Callister |
| 2016/0287432 A1 | 10/2016 | Dabrowiak |
| 2016/0287433 A1 | 10/2016 | Mazzone |
| 2016/0287434 A1 | 10/2016 | Dabrowiak |
| 2016/0287435 A1 | 10/2016 | Pamichev |
| 2017/0035604 A1 | 2/2017 | Dabrowiak |
| 2018/0185192 A1 | 7/2018 | Mazzone |
| 2018/0185193 A1 | 7/2018 | Mazzone |
| 2018/0207024 A1 | 7/2018 | Dabrowiak |
| 2018/0214302 A1 | 8/2018 | Dabrowiak |
| 2018/0214303 A1 | 8/2018 | Dabrowiak |
| 2018/0311072 A1 | 11/2018 | Pamichev |
| 2018/0325725 A1 | 11/2018 | Dabrowiak |
| 2019/0133820 A1 | 5/2019 | Jacobsen |

FOREIGN PATENT DOCUMENTS

| | | |
|---|---|---|
| EP | 0663529 B1 | 5/1997 |
| GB | 2040169 | 8/1980 |
| GB | 1183185 | 2/1985 |
| GB | 2212262 | 7/1989 |
| GB | 2383828 | 7/2003 |
| JP | S 61100243 | 5/1986 |
| JP | 09-215754 | 8/1997 |
| JP | 10-0127777 | 5/1998 |
| JP | 10-305103 | 11/1998 |
| JP | 2001147095 | 5/2001 |
| JP | 2002534160 | 10/2002 |
| JP | 2003028582 | 1/2003 |
| JP | 2003508150 | 3/2003 |
| JP | 2003524507 A | 8/2003 |
| JP | 2008154751 | 7/2008 |
| JP | 2008531114 | 8/2008 |
| JP | 2008539034 A | 11/2008 |
| JP | 2009500066 | 1/2009 |
| JP | 2011505929 | 3/2011 |
| JP | 2011137621 | 7/2011 |
| JP | 2011182849 | 9/2011 |
| JP | 2014023604 A | 2/2014 |
| JP | 2017508509 | 3/2017 |
| JP | 2017511716 | 4/2017 |
| WO | 1990001682 | 2/1990 |
| WO | WO 1993002730 | 2/1993 |
| WO | 1993004727 | 3/1993 |
| WO | 1994000177 | 1/1994 |
| WO | 1994001177 | 1/1994 |
| WO | 95-03680 | 2/1995 |
| WO | 1997025011 | 7/1997 |
| WO | 1998024491 | 6/1998 |
| WO | 1998040017 | 9/1998 |
| WO | 2000010494 | 3/2000 |
| WO | 2001013809 | 3/2001 |
| WO | 0126719 | 4/2001 |
| WO | 2001064146 | 9/2001 |
| WO | 2001076517 | 10/2001 |
| WO | 2001083001 | 11/2001 |
| WO | WO 2005117546 | 12/2005 |
| WO | WO 2006036585 | 4/2006 |
| WO | WO 2009056640 | 5/2009 |
| WO | WO 2010040819 | 4/2010 |
| WO | 2012-175089 | 12/2012 |
| WO | 2014160422 A1 | 10/2014 |
| WO | 2015119670 A1 | 8/2015 |
| WO | 2015119671 A1 | 8/2015 |
| WO | 2015122938 A1 | 8/2015 |

OTHER PUBLICATIONS

American Urethane Inc., "Polyurethane Properties", available Oct. 12, 2010, http://web.archive.org/web/20101012211957/http://americanurethane.com/polyurethane-properties.html.*

Zenith, Natural Rubber / Styrene Butadiene Rubber Sheets, Available Nov. 1, 2011, Accessed at http://web.archive.org/web/20111101235527/http://www.zenithrubber.com/rubber-sheets/nr-sbr-rubber-sheets.htm.*

Christoph Matthias Pistor, Jeremy Thomas Dabrowiak, Christo Pamichev, "Fluid Cassette with Polymeric Membranes and Integral Inlet and Outlet Tubes for Patient Heat Exchange System" file history of related U.S. Appl. No. 14/180,655, filed Feb. 14, 2014.

Jeremy Thomas Dabrowiak, Braig Wendell Pendry, Christop Matthias Pistor, "Patient Heat Exchange System with Two or Only Two Fluid Loops" file history of related U.S. Appl. No. 14/180,719, filed Feb. 14, 2014.

(56) References Cited

OTHER PUBLICATIONS

Jeremy Thomas Dabrowiak, "Heat Exchange System for Patient Temperature Control with Multiple Coolant Chambers for Multiple Heat Exchange Modalities" file history of related U.S. Appl. No. 14/175,545, filed Feb. 7, 2014.
Jeremy Thomas Dabrowiak, Eric Peterson, "Patient Heat Exchange System with Transparent Wall for Viewing Circulating Refrigerant" file history of related U.S. Appl. No. 14/276,202, filed May 13, 2014.
Austin Reid Hendricks, Christo Petrov Pamichev, Venkata Vishnu Gurukula, Jeremy Thomas Dabrowiak, "Heat Exchange System for Patient Temperature Control with Easy Loading High Performance Peristaltic Pump" file history of related U.S. Appl. No. 14/534,718, filed Nov. 6, 2014.
F.W. Behmann, E. Bontke, "Die Regelung der Wärmebildung bei künstlicher Hypothermie", Pflügers Archiv, Bd. 266, S. 408-421 (1958).
F.W. Behmann, E. Bontke, "Intravasale Kühlung", Pflügers Archiv, Bd. 263, S. 145-165 (1956).
Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.
Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).
Jeremy Thomas Dabrowak, Mark Davey, "Serpentine Heat Exchange Assembly for Removable Engagement with Patient Heat Exchange System", file history of related U.S. Appl. No. 14/675,421, filed Mar. 31, 2015.
James Mazzone, "Proximal Mounting of Temperature Sensor in Intravascular Temperature Management Catheter", file history of related U.S. Appl. No. 14/675,452, filed Mar. 31, 2015.
Jeremy Thomas Dabrowiak, Craig Wendell Pendry, Christoph Matthias Pistor, "Cold Plate Design in Heat Exchanger for Intravascular Temperature Management Catheter and/or Heat Exchange Pad", file history of related U.S. Appl. No. 14/675,504, filed Mar. 31, 2015.
Christo Petrov Pamichev, Jeremy Thomas Dabrowiak, "Working Fluid Cassette with Hinged Plenum or Enclosure for Interfacing Heat Exchanger with Intravascular Temperature Management Catheter", file history of related U.S. Appl. No. 14/676,672, filed Apr. 1, 2015.
Christo Petrov Pamichev, Jeremy Thomas Dabrowiak, "Heat Exchange System for Patient Temperature Control With Easy Loading High Performance Peristaltic Pump", file history of related U.S. Appl. No. 14/676,682, filed Apr. 1, 2015.
Jeremy Thomas Dabrowiak, Craig Wendell Pendry, Christoph Matthias Pistor, "Patient Heat Exchange System with Two and Only Two Fluid Loops", related U.S. Appl. No. 14/180,719, Non-Final Office Action dated Jun. 7, 2016.
Christoph Matthias Pistor, Jeremy Thomas Dabrowiak, Craig Wendell Pendry, Christo Pamichev, "Fluid Cassette with Polymeric Membranes and Integral Inlet and Outlet Tubes for Patient Heat Exchange System", related pending U.S. Appl. No. 14/180,655, applicant's response to non-final office action file Jun. 1, 2016.
Jeremy Thomas Dabrowiak, Eric Peterson, "Patient Heat Exchange System with Transparent Wall for Viewing Circulating Refrigerant", related pending U.S. Appl. No. 14/276,202, applicant's response to non-final office action filed Jun. 1, 2016.
Christoph Matthias Pistor, Jeremy Thomas Dabrowiak, Craig Wendell Pendry, Christo Petrov Pamichev, "Fluid Cassette with Polymeric Membranes and Integral Intel and Outlet Tubes for Patient Heat Exchange System", related pending U.S. Appl. No. 14/180,655, non-final office action dated May 18, 2016.

Jeremy Thomas Dabrowiak, Eric Peterson, "Patient Heat Exchange System with Transparent Wall for Viewing Circulating Refrigerant", related pending U.S. Appl. No. 14/276,202, non-final office action dated May 19, 2016.
Jeremy Thomas Dabrowiak, Eric Peterson, "Patient Heat Exchange System with Transparent Wall for Viewing Circulating Refrigerant", related pending U.S. Appl. No. 14/276,202 final office action dated Jul. 15, 2016.
Austin Reid Hendricks, Christo Petrov Pamichev, Venkata Vishnu Gurukula, Jeremy Thomas Dabrowiak, "Heat Exchange System for Patient Temperature Control with Easy Loading High Performance Peristaltic Pump", related U.S. Appl. No. 14/534,718, Non-Final Office Action dated Jul. 25, 2016.
Christoph Matthias Pistor, Jeremy Thomas Dabrowiak, Craig Wendell Pendry, Christo Pamichev, "Fluid Cassette With Polymeric Membranes and Integral Inlet and Outlet Tubes for Patient Heat Exchange System", related U.S. Appl. No. 14/180,655, Final Office dated Sep. 8, 2016.
Jeremy Thomas Dabrowiak, Craig Wendell Pendry, Christoph Matthias Pistor, "Patient Heat Exchange System with Two and Only Two Fluid Loops", related U.S. Appl. No. 14/180,719, Applicant's response to the Non-Final Office Action filed Sep. 7, 2016.
Jeremy Thomas Dabrowiak, "Heat Exchange System for Patient Temperature Control with Multiple Coolant Chambers for Multiple Heat Exchange Modalities", related pending U.S. Appl. No. 14/175,545 non-final office action dated Feb. 12, 2016.
Jeremy Thomas Dabrowiak, "Heat Exchange System for Patient Temperature Control with Multiple Coolant Chambers for Multiple Heat Exchange Modalities", related pending U.S. Appl. No. 14/175,545 applicants response to non-final office action filed May 2, 2016.
Baharlou, "Written Opinion of the International Searching Authority", dated Oct. 12, 2017, from Counterpart PCT application PCT/US2016/024970.
Dabrowiak "Heat Exchange System for Patient Temperature Control with Multiple Coolant Chambers for Multiple Heat Exchange Modalities", related pending U.S. Appl. No. 14/175,545 non-final office action dated Feb. 12, 2016.
Dabrowiak et al., "Fluid Cassette with Tensioned Polymeric Membranes for Patient Heat Exchange System", related pending U.S. Appl. No. 14/180,613, applicant's response to non-final office action filed Jun. 1, 2016.
Dabrowiak et al., "Heat Exchange System for Patient Temperature Control with Multiple Coolant Chambers for Multiple Heat Exchange Modalities" file history of related U.S. Appl. No. 14/175,545, filed Feb. 7, 2014.
Dabrowiak et al., "Patient Heat Exchange System with Transparent Wall for Viewing Circulating Refrigerant" file history of related U.S. Appl. No. 14/276,202, filed May 13, 2014.
Dabrowiak et al., "Patient Heat Exchange System with Transparent Wall for Viewing Circulating Refrigerant", related pending U.S. Appl. No. 14/276,202, applicant's response to non-final office action filed Jun. 1, 2016.
Dabrowiak et al., "Fluid Cassette with Tensioned Polymeric Membranes for Patient Heat Exchange System" file history of related U.S. Appl. No. 14/180,613, filed Feb. 14, 2014.
Dabrowiak et al., "Fluid Cassette with Tensioned Polymeric Membranes for Patient Heat Exchange System" related pending U.S. Appl. No. 14/180,613, non-final office action dated May 19, 2016.
Dabrowiak et al., "Fluid Cassette with Tensioned Polymeric Membranes for Patient Heat Exchange System", related pending U.S. Appl. No. 14/180,613 final office action dated Jul. 15, 2016.
Dabrowiak et al., "Patient Heat Exchange System with Transparent Wall for Viewing Circulation Refrigerant", related pending U.S. Appl. No. 14/276,202, applicant's response to non-final office action filed Aug. 21, 2018.
Dabrowiak et al., "Patient Heat Exchange System With Two and Only Two Fluid Loops", file history of related U.S. Appl. No. 14/180,719, filed Feb. 14, 2014.
Dabrowiak et al., "Patient Heat Exchange System with Two and Only Two Fluid Loops", related U.S. Appl. No. 14/180,719, Non-Final Office Action dated Jun. 7, 2016.

(56) References Cited

OTHER PUBLICATIONS

Dabrowiak et al., "Patient Heat Exchanger System with Transparent Wall for Viewing Circulation Refrigerant", related pending U.S. Appl. No. 14/276,202, non-final office action dated Feb. 21, 2018.

Dabrowiak et al., "Patient Heat Exchange System with Two and Only Two Fluid Loops", related U.S. Appl. No. 14/180,719, Applicant's Response to the Non-Final Office Action filed Sep. 7, 2016.

Dabrowiak, "Heat Exchange System for Patient Temperature Control With Multiple Coolant Chambers for Multiple Heat Exchange Modalities", File History of related pending U.S. Appl. No. 15/332,519, filed Oct. 24, 2016.

Dabrowiak, "Working fluid cassette with hinged plenum or enclosure for interfacing heat exchanger with intravascular temperature management catheter", filed history of related U.S. Appl. No. 14/676,672, filed Apr. 1, 2015.

European Office Action in Application No. 16775853.1, dated Nov. 6, 2019, 5 pages.

International Search Report dated Jun. 25, 2018 in related PCT Application No. PCT/US2018/016752, 4 pages.

International Search Report dated Jun. 25, 2018 in related PCT Application No. PCT/US2018/016754, 4 pages.

Japanese Office Action in Application No. 2018-118084, dated Sep. 2, 2019, 10 pages.

Pistor et al., "Fluid Cassette with Polymeric Membranes and Integral Inlet and Outlet Tubes for Patient Heat Exchange System", related pending U.S. Appl. No. 14/180,655, applicant's response to non-final office action file Jun. 1, 2016.

Wittman-Regis, "Written Opinion of the International Searching Authority", dated Oct. 12, 2017, from counterpart PCT application PCT/US2016/025030.

Chinese Office Action in Application No. 201480077207.7, dated Jul. 3, 2019, 24 pages.

Japanese Office Action in Application No. 2018-160938, dated Jul. 19, 2019, 6 pages.

* cited by examiner

FLUID CASSETTE WITH TENSIONED POLYMERIC MEMBRANES FOR PATIENT HEAT EXCHANGE SYSTEM

FIELD OF THE INVENTION

The present application relates generally to fluid cassettes with tensioned polymeric membranes for patient heat exchange systems.

BACKGROUND OF THE INVENTION

Patient temperature control systems have been introduced to prevent fever in patients in the neuro ICU due to suffering from sub-arachnoid hemorrhage or other neurologic malady such as stroke. Also, such systems have been used to induce mild or moderate hypothermia to improve the outcomes of patients suffering from such maladies as stroke, cardiac arrest, myocardial infarction, traumatic brain injury, and high intracranial pressure. Examples of intravascular heat exchange catheters are disclosed in U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, all of which are incorporated herein by reference.

External patient temperature control systems may be used. Such systems are disclosed in U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference.

SUMMARY OF THE INVENTION

A device includes a frame defining a periphery and an opening, preferably rectilinear and more preferably substantially square, bounded on at least three sides by the periphery. The frame is configured for being closely received between two plates, referred to herein as "cold plates" because in cooling mode they are cold, and has at least a fluid inlet and a fluid outlet both establishing respective fluid passageways through the frame into the opening. The fluid inlet and outlet are configured for fluid communication with respective fluid return and supply lines associated with a patient-engageable heat exchange member. A polymeric membrane assembly is connected to the frame in tension, preferably in biaxial tension (tension in both an x-direction and a y-direction). The membrane assembly blocks the opening and includes a first membrane parallel to a second membrane with a space therebetween. The fluid inlet and fluid outlet of the frame communicate with the space between the membranes.

Without limitation, the heat exchange member can include an intravascular heat exchange catheter or a heat exchange pad externally engageable with a patient or a peritoneal lavage device.

In example embodiments the space between the membranes is expandable when filled with working fluid circulating from the heat exchange member. Each membrane may be no more than two mils (0.002") thick and may be between one mil and two mils in thickness (0.001"-0.002").

The opening may be substantially square in that it defines a top, a bottom edge spaced from and parallel to the top, a left side extending between the top and bottom, and a right side extending between the top and bottom and parallel to the left side, with the left and right sides defining a first length, the top and bottom defining a second length, and the first length being equal to the second length±ten percent of the second length. Indeed, the first length can be approximately equal to the second length. However, other shapes such as trapezoidal may be used, in particular with a bottom edge slightly longer than the top edge.

Both membranes of the membrane assembly may be disposed in tension within the opening. Plural posts may be arranged on the frame, and at least portions of the membrane assembly can be stretched over the posts and engaged with the posts to hold the membrane assembly in tension within the opening.

In example implementations the membrane assembly defines a rectilinear border juxtaposed with the frame. The border includes the first and second membranes and at least one reinforcing layer engaged with the first and second membranes and preferably not extending radially inwardly past the border. The membranes may be stretchable to at least 25% elongation. The device may be used in combination with the cold plates and/or the heat exchange member.

In another aspect, an apparatus includes a working fluid chamber defined by two and only two membranes closely spaced from each other, and a hollow frame bordering at least portions of the working fluid chamber and holding the membranes in tension. The hollow frame defines at least one fluid passageway through which fluid can pass into and/or out of the working fluid chamber. When the apparatus is disposed between heat exchange surfaces of a heat exchanger and working fluid fills the working fluid chamber, the working fluid chamber expands against the heat exchange surfaces to facilitate heat exchange with the working fluid.

In another aspect, a method includes stretching first and second polymeric membranes over supports on a first frame half, and engaging the first frame half with a second frame half to establish a cassette receivable between two cold plates. The frame has fluid passageways into a space between the membranes such that the frame is configured for fluid communication with fluid return and supply lines associated with a patient-engageable heat exchange member.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
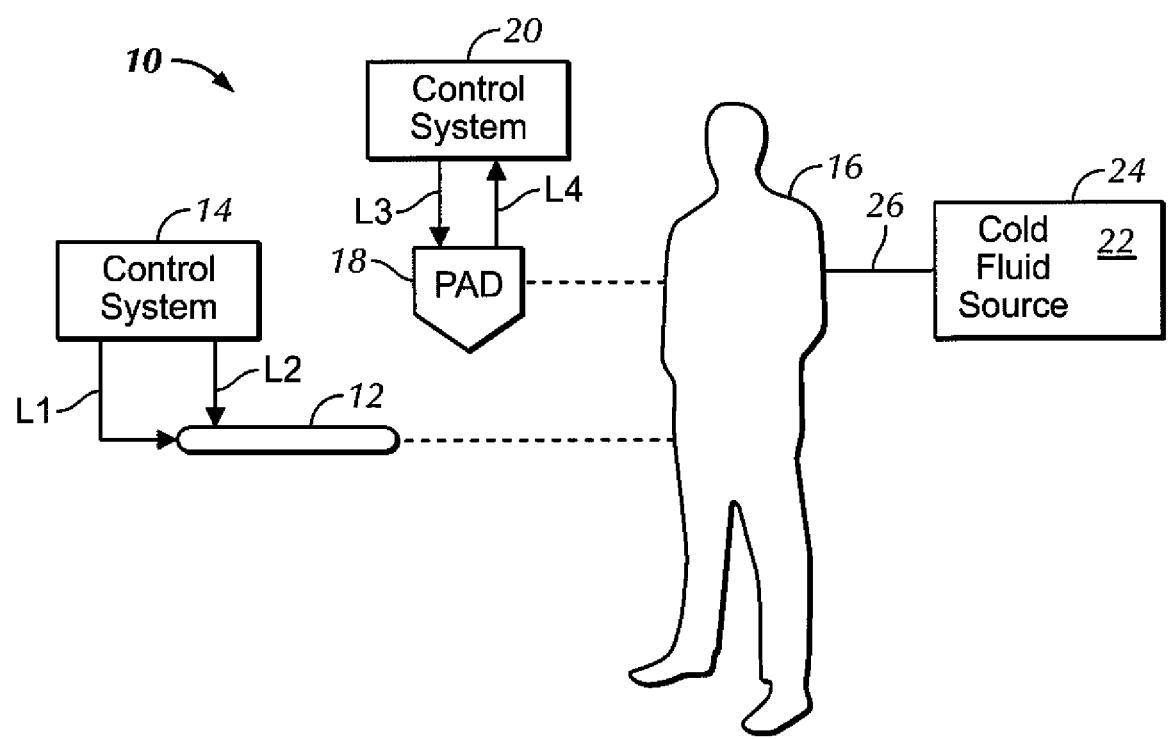
FIG. 1 is a schematic view of a non-limiting system in accordance with the present invention.

Referring initially to FIG. 1, in accordance with present principles, a system 10 may include an intravascular heat exchange catheter 12 controlled by a control system 14 to control patient temperature, e.g., to prevent the patient 16 from becoming febrile or to induce therapeutic hypothermia in the patient 16. In the catheter, working fluid (also referred to as "coolant") such as but not limited to saline circulates (typically under the influence of a pump in the controller) in a closed loop from the control system 14, through a fluid supply line L1, through the catheter 12, and back to the system 14 through a fluid return line L2, such that no coolant enters the body. While certain preferred catheters are disclosed below, it is to be understood that other catheters can be used in accordance with present principles, including, without limitation, any of the catheters disclosed above or in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,325,818, 6,409,747, 6,368,304, 6,338,727, 6,299,599, 6,287,326, 6,126,684. The catheter 12 may be placed in the venous system, e.g., in the superior or inferior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by a pad controller 20 in accordance with principles set forth in the external pad patents to exchange heat with the patient 16, including to induce therapeutic mild or moderate hypothermia in the patient in response to the patient presenting with, e.g., cardiac arrest, myocardial infarction, stroke, high intracranial pressure, traumatic brain injury, or other malady the effects of which can be ameliorated by hypothermia. The pad 18 may receive working fluid from the system 14 through a fluid supply line L3, and return working fluid to the system 14 through a fluid return line L4. Note that in some embodiments, the systems 14, 20 are established in a single assembly.

To cool the patient while awaiting engagement of the catheter 12 and/or pad 18 with the patient, cold fluid 22 in a cold fluid source 24 may be injected into the patient and in particular into the patient's venous system through a pathway 26. Without limitation, the pathway 26 may an IV line, the source 24 may be an IV bag, and the fluid 22 may be chilled saline, e.g., saline at the freezing point or slightly warmer. Or, the source may be a syringe, and the saline can be injected directly into the bloodstream of the patient.

Figure 2:
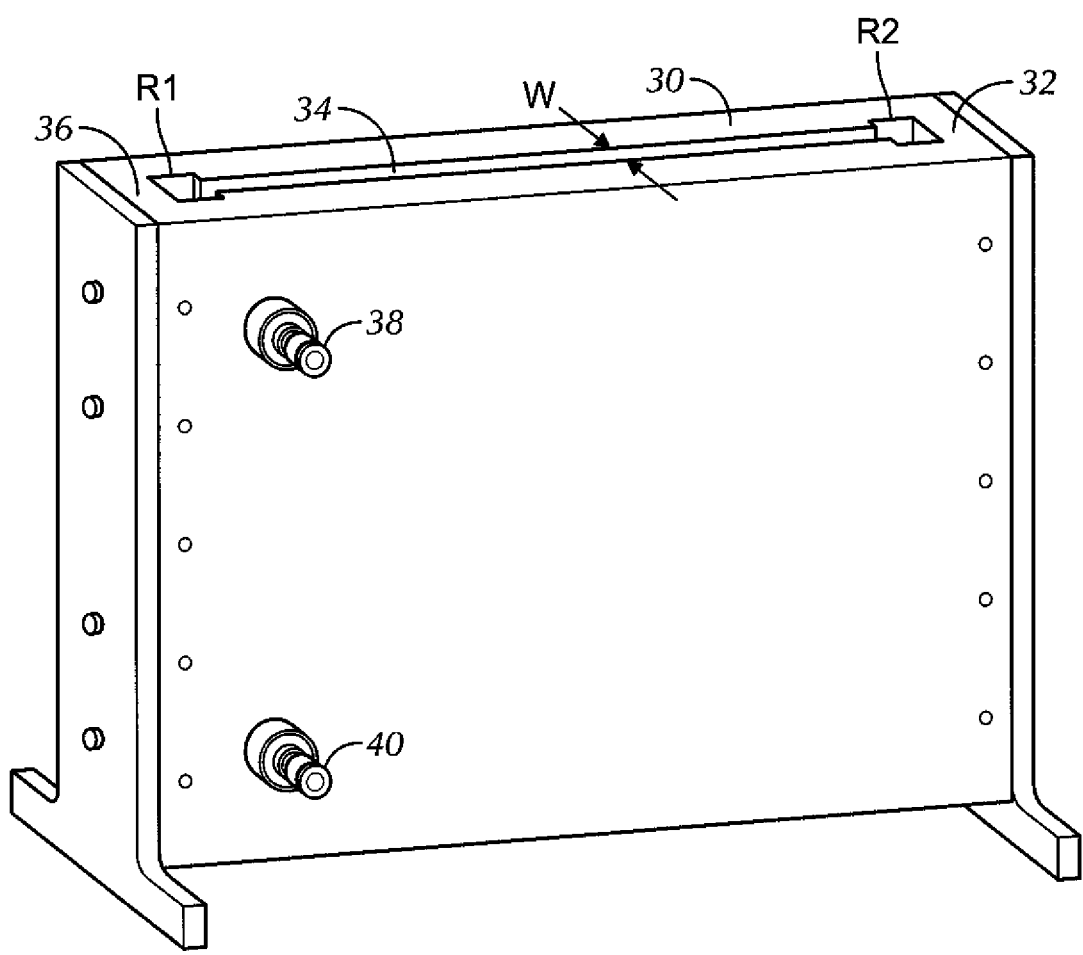
FIG. 2 is a perspective view of an example working fluid cassette holder portion of a heat exchange system.

Now referring to FIG. 2, a portion of either of the heat exchangers in the control systems 14, 20 is shown which includes at least two cold plates 30, 32 defining a cassette slot 34 between them. In one embodiment, the width "W" of the slot 34 is less than forty mils (0.040"), and may be between twenty nine mils and thirty one mils (0.029"-0.031"). In a specific example the width "W" may be thirty mils.

The cold plates 30, 32 may be made of metal, and can be rectilinear as shown and indeed may be nearly square. The cold plates 30, 32 may abut each other along left and right side walls 36, with elongated vertical cassette frame receptacles R1 and R2 being located immediately inboard of the respective side walls 36 and with the slot 34 extending between the walls 36 and terminating at the receptacles R1, R2 as shown. The frame receptacles R1, R2 are wider than the slot 36.

In the example shown, refrigerant inlet and outlet tubes 38, 40 extend through at least one of the cold plates 32 to communicate refrigerant from a compressor into a refrigerant passageway in the cold plate. Each cold plate may have its own refrigerant inlet and outlet tubes, or, in the embodiment shown, only one cold plate may be formed with refrigerant inlet and outlet tubes and the other cold plate either thermally coupled to the cold plate in which the refrigerant flows and/or receiving refrigerant from the other cold plate through passageways formed through one or both of the side walls 36.

Figure 3:
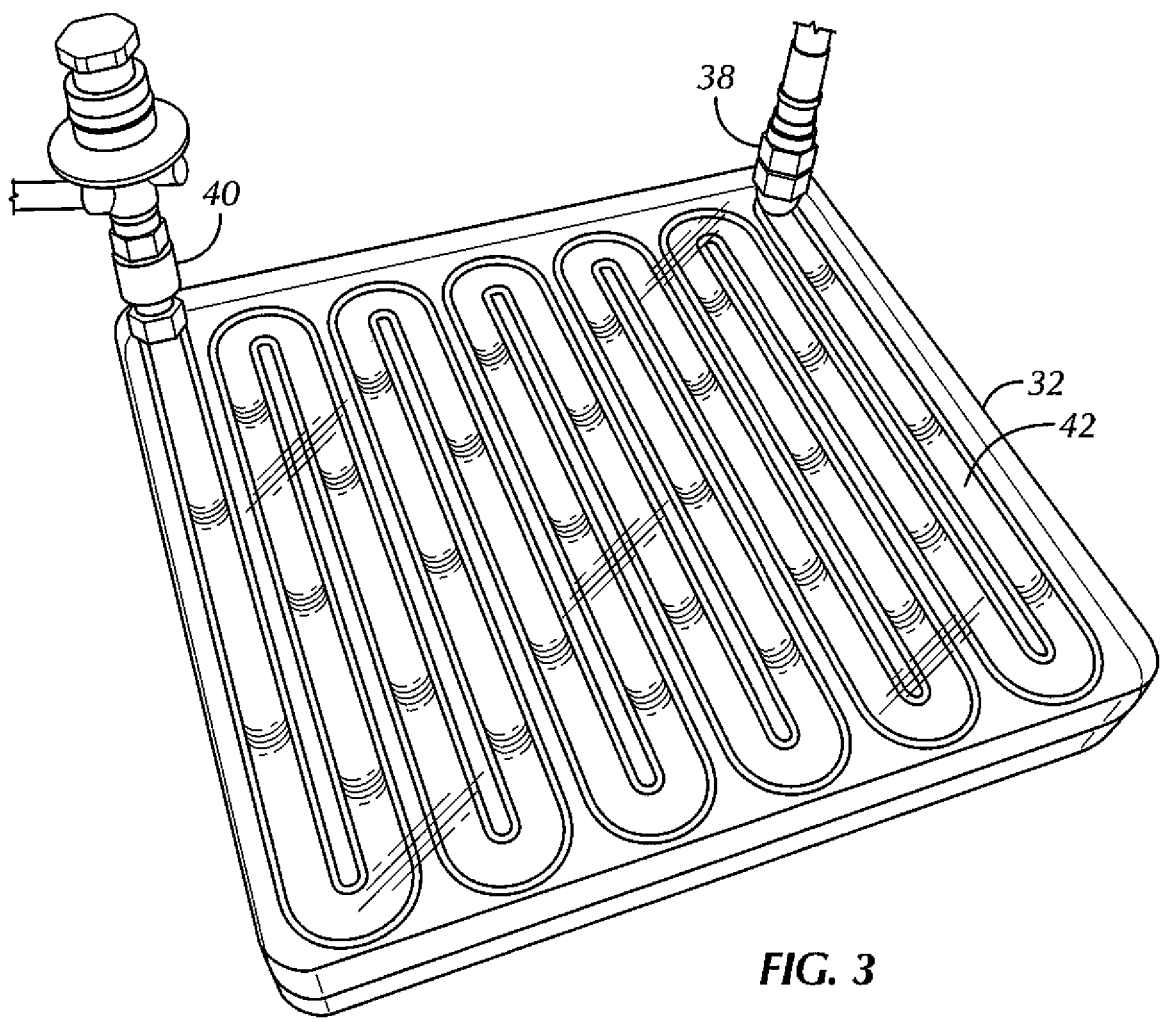
FIG. 3 is a perspective view of one half of the cassette holder shown in FIG. 2, with the opaque metal inner surface shown in transparency to reveal the serpentine refrigerant passageway.

FIG. 3 shows details of an example cold plate 32 looking at the inner surface in transparency, it being understood that the inner surface typically is metal and that the serpentine refrigerant passageway 42 shown in FIG. 3 typically would not be visible to the human eye. In any case, the example refrigerant passageway that fluidly connects the refrigerant inlet 38 to the refrigerant outlet 40 may be serpentine-shaped as shown, or may be some other shape or pattern such as a herringbone pattern a wave pattern, etc.

Figure 4:
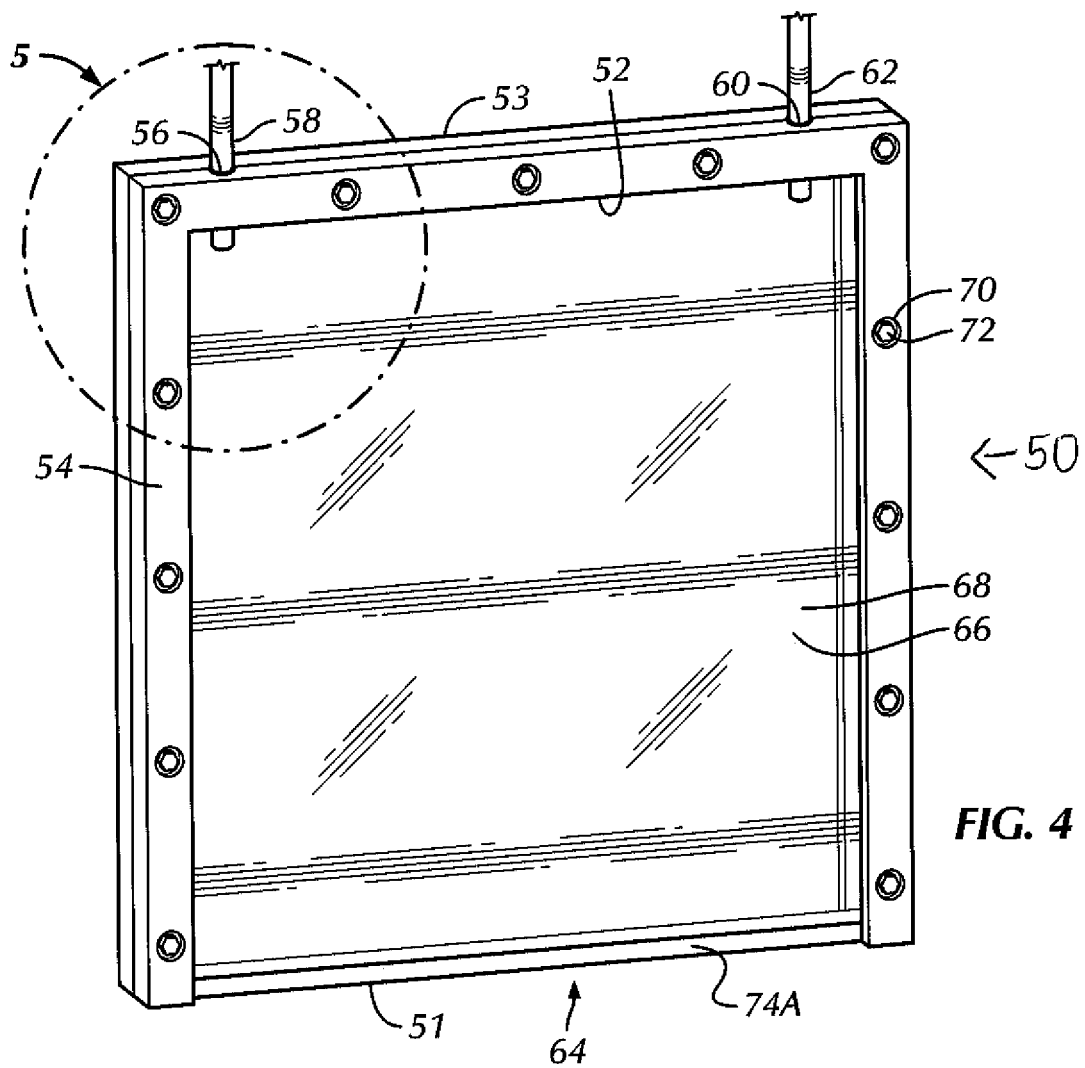
FIG. 4 is a perspective view of an example working fluid cassette configured to engage the cassette holder shown in FIGS. 2 and 3.

FIG. 4 shows an example working fluid cassette 50 according to present principles. The cassette 50 is configured to fit snugly into the slot 34 and cassette frame receptacles R1, R2 defined between the cold plates 30, 32. Working fluid such as saline from a patient-engageable heat exchange member such as the catheter 12 or pad 18 flows through the cassette 50 in operation, with the working fluid exchanging heat with the refrigerant in the cold plates. In example embodiments, the cassette 50 is a low cost single-use disposable item that can contain, e.g., sterile saline which circulates through the catheter 12. The cassette may be placed by a medical caregiver in the slot 34 between the cold plates 30, 32 and the membrane portion which defines a space or working fluid chamber through which the example saline flows inflates when the working fluid flows through it, achieving thermal contact with the cold plates 30, 32.

In the example shown, the cassette 50 includes a frame 52 defining a periphery and a preferably rectilinear opening bounded as shown on at least three sides by the periphery of the frame. In the non-limiting example shown, the frame includes an elongated parallelepiped-shaped top rail 53 and elongated parallelepiped-shaped left and right side rails 54 parallel to each other and perpendicular to the top rail 32. The example frame 52 may have a metal strip or bottom rail 51 opposite the top rail and connected to the left and right side rails to support the membrane and facilitate placing the membrane in biaxial tension. In any case, the example frame 52 is rectilinear and is configured for being closely received between the two cold plates 30, 32, with the side rails 54 slidably engageable with the frame receptacles R1, R2 between the cold plates 30, 32 and with the below-described membrane assembly passed through the slot 36 to be in close juxtaposition with the refrigerant channels in the cold plates.

Figure 5:
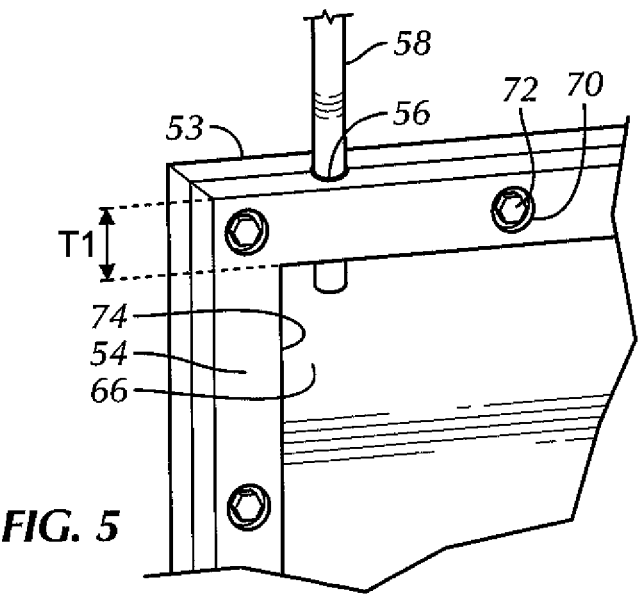
FIG. 5 is a close up perspective view of the cassette shown in FIG. 4, illustrating an inlet tube extending partially down into the stretched membrane chamber, it being understood that an opposed outlet tube may be similarly disposed on the opposite side of the cartridge and that both the inlet and outlet tubes may extend any length down their respective sides in the cassette.
Figure 4A:
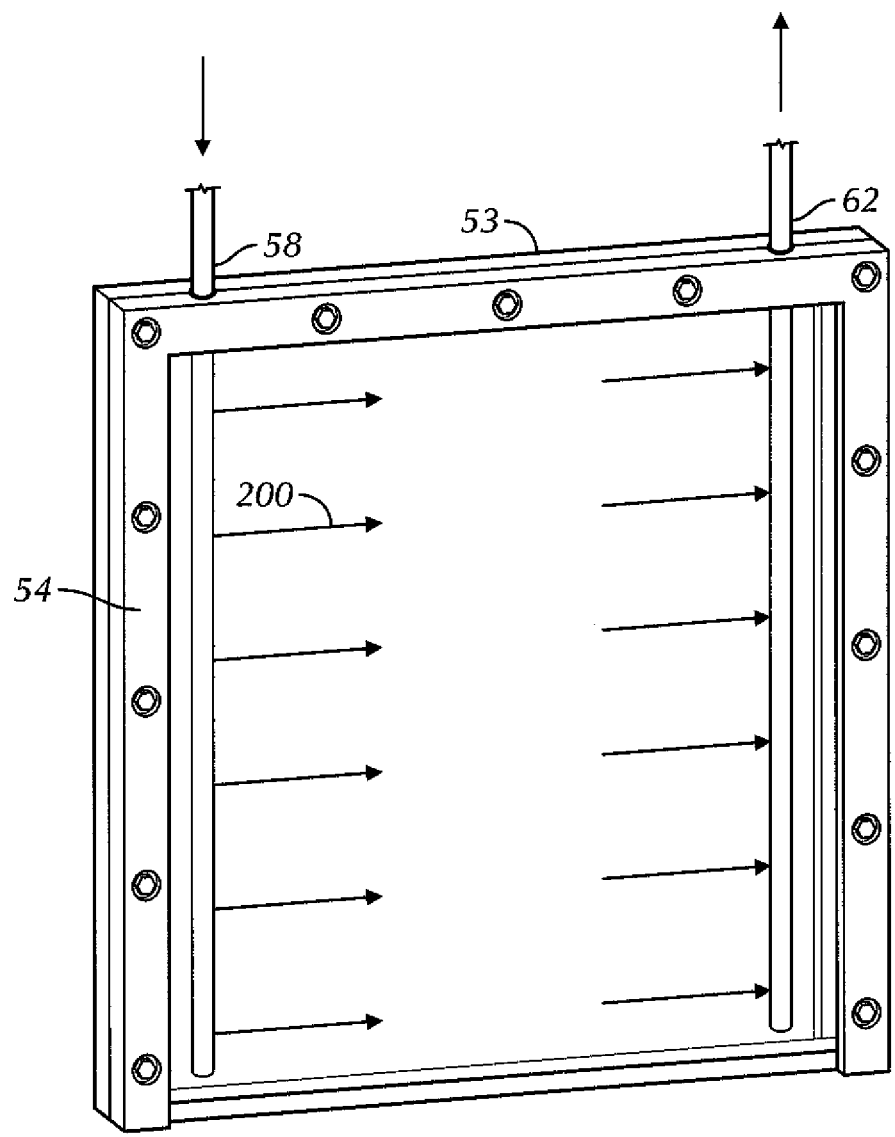
FIG. 4A is similar to FIG. 4, showing the inlet and outlet tubes extending from the top to the bottom of the membrane assembly.

In cross-references to FIGS. 4 and 5, the frame, in the example shown, the top rail 53 thereof, is formed with a fluid inlet 56 in which an inlet tube 58 has been disposed and a fluid outlet 60 in which an outlet tube 62 has been disposed. Both the inlet and outlet establish respective fluid passageways through the frame into the opening. The inlet and outlet tubes 58, 62 may be engaged with the fluid return and supply lines L3, L4 that are associated with the catheter 12. The tubes 58, 62 may terminate at just below the top rail 53 (FIG. 4), or they may extend any desired length down to the bottom of the assembly, i.e., the tubes 58, 62 may extend almost the entire length of the left and right side rails 54, ending just above the below-described bottom seam of the membrane assembly (FIG. 4A). A combination of FIGS. 4 and 4A may be used in which one tube (e.g., the inlet tube) terminates just below the top rail 53 while the other tube (e.g., the outlet tube) ends just above the below-described bottom seam. Or, the outlet tube may terminate just below the top rail 53 while the other inlet tube can end just above the below-described bottom seam. By terminating at least one tube near the bottom of the membranes, evacuation of coolant from between the membranes is facilitated, which facilitates easier removal of the cassette from between the cold plates. A longer "tube" can be established by placing a shorter thinner tube within a longer larger tube which is sealed to the perimeter of the membranes.

Indeed, a polymeric membrane assembly 64 is connected to the frame 52, blocking the opening that is bounded on four sides by the frame as shown. The membrane assembly includes a first membrane 66 that is parallel to and closely spaced from a second membrane 68, leaving a space therebetween which establishes a working fluid chamber. The fluid inlet 56 and fluid outlet 60 communicate with the space between the membranes 66, 68. At least one and preferably both of the membranes 66, 68 are disposed in tension in the opening. The space between the membranes is expandable when filled with working fluid.

In one example, each membrane is no more than two mils (0.002") thick and more preferably is between one mil and two mils in thickness (0.001"-0.002"), inclusive. The example preferred membranes 66, 68 are co-extensive with the opening and like the opening are more or less square, with the length of top and bottom edges of the example membranes being approximately equal (within ±10% and more preferably within ±5%) of the lengths of the left and right edges of the membranes. In other embodiments instead of a square (1:1) aspect ratio, an aspect ratio of up to 1:1.5 may be used. The working fluid chamber between the membranes is also rectilinear and in the preferred embodiment no obstructions exist between the membranes, meaning the working fluid chamber is a complete rectilinear, more or less square chamber.

Owing to the thinness of the membranes 66, 68 and the closeness of the cold plates 30, 32 to each other and to the membrane assembly between them when the cassette is engaged with the cold plates, the system shown in the figures affords low impedance of heat transfer between the refrigerant circulating in the cold plates and the working fluid circulating between the membranes 66, 68. The working fluid chamber between the membranes inflates due to back-pressure generated by working fluid flow, eliminating or reducing the need for a moving mechanism in the cold plates. Moreover, the narrow slot 34 between the two cold plates provides better heat transfer by reducing the conductive path length between the cold plates and the working fluid. The frame allows for ease of handling, such as insertion and removal of the cassette with/from the cold plates.

With respect to the example working fluid chamber between the membranes 66, 68 having a width-to-length aspect ratio near 1:1 (i.e., square or nearly so), the amount of backpressure required to induce working fluid flow through heat exchanger is reduced compared to a less square configuration. This reduces the amount of work that a working fluid pump must perform, which is desirable for two reasons. One, since the pump may be disposable, lower performance requirements translate into a lower cost disposable and quieter system. For instance, peristaltic roller pumps offer quiet operation and a low-cost disposable element, but operate most efficiently when only modest pressures are required. Two, lowering the working fluid pump work reduces the amount of heat transferred into the working fluid by the pump itself. Also, a low width/length aspect ratio results in slower working fluid velocity which reduces amount of mixing, but this otherwise desirable (from a heat exchange standpoint) effect is negligible in the present example system since the Reynolds numbers are typically <1000, suggesting a laminar flow regime. Furthermore, a low width/length aspect ratio significantly reduces the number of bends (or "corners") in the fluid flow path. These bends are areas of mixing for the fluid which promotes heat transfer. Without them, a fluid boundary layer builds up. However, this effect is offset herein by maintaining a narrow slot between the cold plates. This way the primary heat transfer mechanism is by conduction, but the conduction path length (and therefore boundary layer) is small, resulting in a relatively high rate of heat transfer.

In preferred examples, the membranes 66, 68 are stretched under tension during assembly to the frame, preferably biaxially (i.e., in tension between the top and bottom rails 53, 51 and also in tension between the left and right side rails 54). This tension can be maintained over the shelf life of the product. Pretensioning minimizes wrinkles in material, which is beneficial because wrinkles can impede working fluid flow and create air gaps which reduce heat transfer between the working fluid and cold plates. Wrinkles can also complicate insertion of the membrane assembly into the narrow slot 34.

To establish pre-tensioning of the membranes, the frame may be made in halves and posts such as threaded fasteners 70 (FIG. 5) can extend transversely to one half of the frame, with the membranes 66, 68 being stretched over the posts and holes made in the membranes to receive the posts. The other half of the frame is then positioned to sandwich a rectilinear border portion 74 (only the innermost portion of which is shown in FIG. 5) of the membrane assembly between the frame halves, and a closure such as respective nuts 72 engaged with the posts 70 to hold the frame halves together with the membrane assembly held in tension between the frame halves. FIG. 4 shows that the working fluid chamber is closed off at the bottom by a bottom seam 74A of the membrane assembly, which is part of the border portion 74. In addition to applying tension to avoid wrinkling during use, additional posts may be used to avoid wrinkling during the welding process, improving the quality of the weld joints.

In the border portion 74, at least one and preferably more layers of polymer film may be used to reinforce the membranes 66, 68 to establish welded seams through which (at the sides of the membrane assembly) the post holes are formed, allowing for easier fabrication. By placing reinforcing layers on the border portion 74 only, the central "window" of the membrane assembly consists only of a single thin layer membrane between the working fluid and one of the cold plates 30, 32 to minimize impeding heat transfer. A die-cut reinforcement layer may be used which reinforces the entire perimeter with one piece of material.

In some examples, the polymer membranes 66, 68 are highly stretchable, at least greater than 25% elongation. This allows the membranes to change from the empty flat state shown in FIGS. 4 and 5 to an inflated shape (within the slot 34 between the cold plates) without wrinkling. It also allows the membranes to easily conform to features on the faces of the cold plates.

Additionally, the membranes may be made of a material which can also be made into tubing. Tubes such as the inlet and outlet tubes 58, 62 shown in FIG. 4 can then be thermally welded (e.g., using RF sealing) to the membranes, which is more reliable and quicker than adhesive bonding. The membranes 66, 68 need not provide their own lateral support because the cold plates 32, 34 and frame provide the support for the inflated membrane assembly, allowing it to withstand the pressure generated as a result of working fluid flowing through between the membranes. Structural features such as raised bumps, concavities, raised ribs, and so on may be located on the cold plates to optimize heat transfer. This can be economically advantageous because the cold plates are reusable components. Manifolds can be cut into the cold plates to even out the distribution of saline flow.

Figure 6:
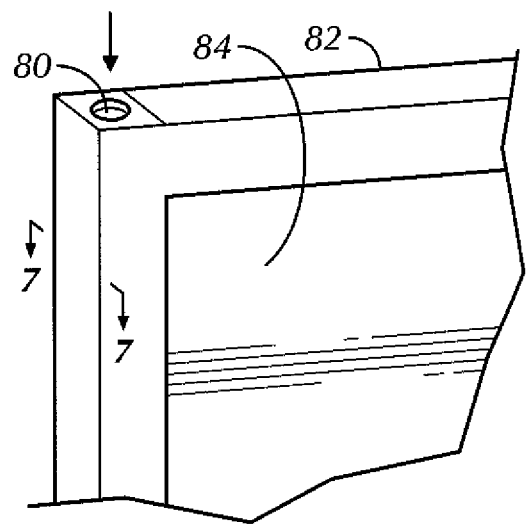
FIG. 6 is a perspective view of an alternate cassette in which the inlet and outlet tubes are formed in the frame of the cassette, with portions broken away for clarity.
Figure 7:
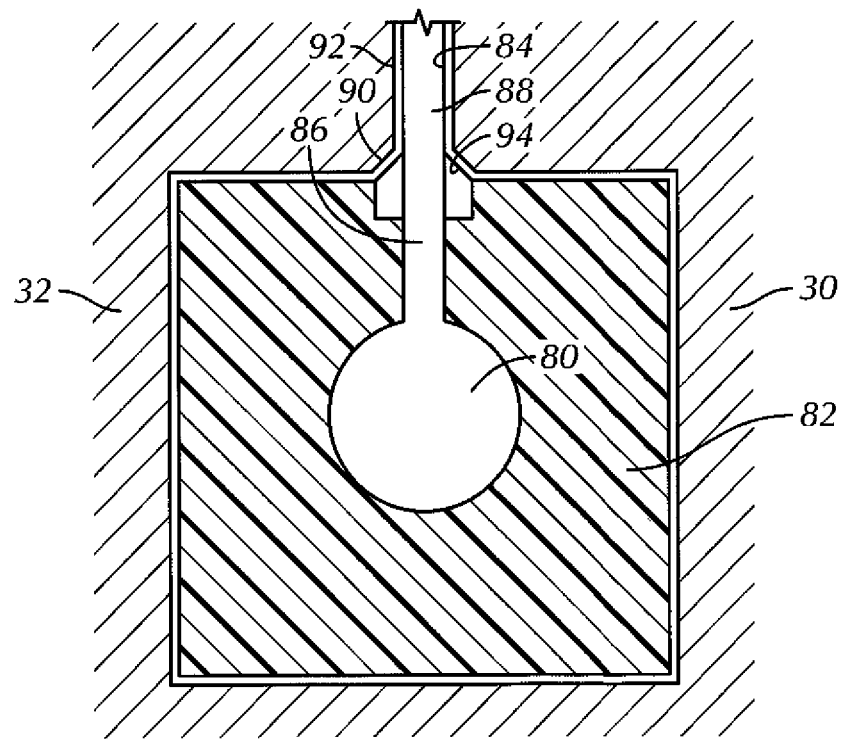
FIG. 7 is a view in partial cross-section as seen along the line 7-7 in FIG. 6, with portions broken away for clarity, and assuming the cassette is engaged between the cold plates.

FIGS. 6 and 7 show that alternatively, a working fluid inlet 80 may be formed in the left rail of a frame 82 holding a membrane assembly 84 in tension. It is to be understood that a working fluid outlet may be formed in the right rail of the frame 82. The inlet 80 and outlet may extend almost the entire length of the rail if desired or may extend only part way down the rail. In any case one or more lateral channels 86 extend from the inlet 80 to the working fluid chamber 88 of the membrane assembly 84 to establish fluid communication between the inlet (and outlet) of the frame 82 and the working fluid chamber. If desired, the cold plates 30, 32 may be formed with a chamfer 90 at the start of the slot 92 in which the membrane assembly 84 is disposed, with a complementarily shaped chamfer 94 being formed in the rail of the frame 82, to accommodate any "ballooning" of the membrane assembly 84 at the frame/membrane interface as the saline flows out of the frame into the membrane assembly.

While the particular FLUID CASSETTE WITH TENSIONED POLYMERIC MEMBRANES FOR PATIENT HEAT EXCHANGE SYSTEM is herein shown and described in detail, the scope of the present invention is to be limited by nothing other than the appended claims.

What is claimed is:

1. A device, comprising:
   a frame defining a periphery and an opening bounded on at least three sides by the periphery, the frame being configured for being closely received between two cold plates, the frame having a segment with at least a fluid inlet and a fluid outlet both establishing respective fluid passageways through the segment of the frame into the opening, the fluid inlet and outlet being configured for fluid communication with respective fluid return and supply lines associated with a patient-engageable heat exchange member;
   a membrane assembly connected to the frame and blocking the opening, the membrane assembly including a first membrane parallel to a second membrane with a space therebetween,
   an inlet tube and an outlet tube respectively engaged with the fluid inlet and the fluid outlet, the outlet tube terminating just below the segment of the frame, and the inlet tube extending to near a bottom of the frame, the inlet tube comprising a thinner tube within a larger tube, wherein in operation each of the thinner tube and the larger tube are configured for liquid return from the patient-engageable heat exchange member through the frame such that liquid can flow separately in each of the thinner tube and the larger tube.

2. The device of claim 1, comprising the heat exchange member, wherein the heat exchange member includes an intravascular heat exchange catheter.

3. The device of claim 1, comprising the heat exchange member wherein the heat exchange member includes a heat exchange pad externally engageable with a patient.

4. The device of claim 1, wherein the space is expandable when filled with working fluid comprising the liquid circulating from the heat exachange member.

5. The device of claim 1, wherein each membrane is no more than two millimeters thick.

6. The device of claim 1, wherein the membranes are disposed in biaxial tension in the frame.

7. The device of claim 1, comprising a plurality of posts extending trnasversely away from one or more surfaces of the frame, at least portions of the membrane assembly being stretched over the posts and having holes to receive respective posts to hold the membrane assembly in tension within the opening.

8. The device of claim 7, comprising at least one closure engaged with at least one of the posts to hold a first half of the frame with which the posts are engaged to a second half of the frame with the membrane assembly held in tension between the first and second halves of the frame.

9. The device of claim 1, wherein the opening defines a top, a bottom edge spaced from and parallel to the top, a left side extending between the top and bottom, and a right side extending between the top and bottom and parallel to the left side, the left and right sides defining a first length, the top and bottom defining a second length, and the first length being equal to the second length +(plus or minus) ten percent of the second length.

10. The device of claim 9, wherein the first length is approximately equal to the second length.

11. The device of claim 1, wherein both membranes of the membrane assembly are disposed in tension within the opening.

12. The device of claim 1, wherein the membrane assembly defines a rectilinear border juxtaposed with the frame, the border including the first and second membranes and at least one reinforcing layer engaged with the first and second membranes to at least in part establish the border.

13. The device of claim 1, wherein the membranes are stretchable to at least 25% elongation.

14. The device of claim 1, comprising the cold plates.

15. The device of claim 14, comprising the heat exchange member.

16. An apparatus comprising:
   a working fluid chamber defined by membranes closely spaced from each other; and
   a frame bordering at least portions of the working fluid chamber and holding the membranes, the frame defining fluid passageways through which fluid can pass into and/or out of the working fluid chamber, the frame being configured for being closely received between two cold plates;

at least one inlet tube and at least one outlet tube extending into the working fluid chamber through the fluid passageways, the at least one inlet tube configured for fluid communication with a fluid return line associated with a patient-engageable heat exchange member, and the at least one outlet tube configured for fluid communication with a fluid supply line associated with the patient-engageable heat exchange member; and the inlet tube comprising a thinner tube within a larger tube, wherein in operation each of the thinner tube and the larger tube are configured for liquid return from the patient-engageable heat exchange member through the frame such that liquid can flow separately in each of the thinner tube and the larger tube.

17. The apparatus of claim 16, wherein the frame is substantially square and the membranes are polymeric membranes each being no more than two millimeters thick.

18. The apparatus of claim 16, wherein the fluid passageway defines a top, a bottom edge spaced from and parallel to the top, a left side extending between the top and bottom, and a right side extending between the top and bottom and parallel to the left side, the left and right sides defining a first length, the top and bottom defining a second length, the first length being equal to the second length plus or minus ten percent of the second length.

19. The apparatus of claim 16, wherein the membranes define a rectilinear border juxtaposed with the frame, the border including the first and second membranes and at least one reinforcing layer engaged with the first and second membranes and not extending radially inwardly past the border.

20. The apparatus of claim 16, comprising plural posts extending transversely away from one or more surfaces of the frame, at least portions of the membranes being stretched over the posts and having holes to receive respective posts to hold the membranes tension.

21. The apparatus of claim 20, comprising:
at least one closure engaged with at least one of the posts to hold a first half of the frame with which the posts are engaged to a second half of the frame, with at least the first one of the membranes held in tension between the first and second halves of the frame.

* * * * *

UNITED STATES PATENT AND TRADEMARK OFFICE
CERTIFICATE OF CORRECTION

PATENT NO. : 11,033,424 B2
APPLICATION NO. : 14/180613
DATED : June 15, 2021
INVENTOR(S) : Jeremy Thomas Dabrowiak et al.

It is certified that error appears in the above-identified patent and that said Letters Patent is hereby corrected as shown below:

On the Title Page

Column 2, Line 1, Item (56) under "OTHER PUBLICATIONS", delete "Properities" and insert -- Properties --

Column 2, Lines 1-2, Item (56) under "OTHER PUBLICATIONS", delete "Characterisitics," and insert -- Characteristics, --

Column 2, Line 3, Item (56) under "OTHER PUBLICATIONS", delete "properites" and insert -- properties --

In the Claims

Column 8, Line 20, Claim 4, delete "exachange" and insert -- exchange --

Column 8, Line 26, Claim 7, delete "trnasversely" and insert -- transversely --

Column 8, Line 34, Claim 8, delete "frame" and insert -- frame, --

Column 8, Line 42, Claim 9, delete "+" and insert -- ± --

Column 10, Line 15, Claim 20, after "membranes", insert -- in --

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*